US007993670B2

(12) United States Patent
Simonson et al.

(10) Patent No.: US 7,993,670 B2
(45) Date of Patent: Aug. 9, 2011

(54) MEDICAL PAD, AND METHOD FOR MAKING AND USING

(75) Inventors: Richard M. Simonson, New York, NY (US); Theodore McAllister, San Antonio, TX (US); Richard R. Suchanec, Newark, DE (US); Daniel A. White, La Grange, TX (US)

(73) Assignee: General Wound Kare, Inc., New York, NY (US)

( * ) Notice: Subject to any disclaimer, the term of this patent is extended or adjusted under 35 U.S.C. 154(b) by 1059 days.

(21) Appl. No.: 10/525,323

(22) PCT Filed: Aug. 20, 2003

(86) PCT No.: PCT/US03/25897

§ 371 (c)(1), (2), (4) Date: Sep. 20, 2005

(87) PCT Pub. No.: WO2004/028400

PCT Pub. Date: Apr. 8, 2004

(65) Prior Publication Data

US 2006/0062829 A1 Mar. 23, 2006

(51) Int. Cl.

| | |
|---|---|
| ***A61K 9/70*** | (2006.01) |
| ***A61K 31/44*** | (2006.01) |
| ***A61K 31/47*** | (2006.01) |
| ***A61K 31/135*** | (2006.01) |
| ***A41D 19/00*** | (2006.01) |
| ***A61F 13/02*** | (2006.01) |

(52) U.S. Cl. ........ 424/443; 514/283; 514/297; 514/310; 514/649; 427/2.3; 427/2.31

(58) Field of Classification Search .................. 424/443; 514/310, 283, 297, 649; 427/2.3, 2.31
See application file for complete search history.

(56) References Cited

U.S. PATENT DOCUMENTS

| | | | | |
|---|---|---|---|---|
| 3,635,652 | A | 1/1972 | Streck | |
| 3,961,629 | A * | 6/1976 | Richter et al. | 604/369 |
| 3,978,855 | A | 9/1976 | McRae et al. | |
| 4,045,238 | A | 8/1977 | Battista et al. | |
| 4,541,426 | A | 9/1985 | Webster | |
| 5,811,471 | A * | 9/1998 | Shanbrom | 521/141 |
| 5,973,221 | A | 10/1999 | Collyer et al. | |
| 6,361,786 | B1 | 3/2002 | Shanbrom | |
| 7,030,203 | B2 * | 4/2006 | Mosbey et al. | 526/318.44 |
| 2003/0149106 | A1 | 8/2003 | Mosbey et al. | |

FOREIGN PATENT DOCUMENTS

| | | |
|---|---|---|
| EP | A1-0 106 439 | 4/1984 |
| EP | A-0 181 184 | 5/1986 |
| EP | A2-0 256 893 | 2/1988 |
| EP | A1-0 541 390 | 5/1993 |
| GB | A-1 450 201 | 9/1976 |
| WO | WO91/01706 A | 2/1991 |
| WO | WO 01/60423 A | 8/2001 |
| WO | WO 03/002163 A | 1/2003 |

OTHER PUBLICATIONS

Drug Facts and Comparisons, 1994 edition, Wolters Kluwer Co. p. 2478.*

* cited by examiner

*Primary Examiner* — Raymond Henley, III
(74) *Attorney, Agent, or Firm* — William H. Holt

(57) ABSTRACT

A germicidal absorptive material for use in surgical packings, wound bandages, sanitary tampons and bed sore prevention and/or treatment uses is provided by a foam-like matrix of hydrophilic polyurethane polymer to which application-specific loads of a germicidal disinfectant dye have been made. Polyurethane polymer of various densities and thicknesses exhibits an exceptional ability to absorb different levels of a number of disinfectant dyes, both basic and acidic, such as gentian violet and methylene blue, respectively. The relationship between dye-load and application-specific uses permits a totally-bound gentian violet pad to be used as a conventional bandage or pad on a surface wound with the capability of preventing the incursion of external pathogens from entering the wound through the pad, where the pathogens are killed by the bound-dye. The wound exudate is absorbed safely by the pad, where wound-originating pathogens are also killed. When the loaded dye's concentration is saturated by exceeding the bound-dye limit, the limited free-dye is available to be delivered to the wound, particularly deep wounds, to rapidly kill pathogens in the wound. The free dye delivery pad can then be replaced by the bound-dye pad to absorb the wound exudate.

6 Claims, No Drawings

MEDICAL PAD, AND METHOD FOR MAKING AND USING

TECHNICAL FIELD

The invention relates to the field of medicine and more particularly to medical pads which include medicaments for treating, protecting and healing wounds of all types, large and small, deep and shallow, infected or non-infected. and to the methods or processes for manufacturing the pads, including the preparation of and application of preferred medicaments, and methods of use depending upon the type of wound, injury, sore incision and the like.

BACKGROUND ART

U.S. Pat. No. 5,811,417 granted to Edward Shanbrom, of Santa Ana, Calif. on Sep. 22, 1998, and entitled "Disinfectant Plastic Sponge Material" discloses a germicidal absorptive material for purposes similar to those of the present invention. The patent also sets forth background information to earlier disclosures in the same field for producing bandages and the like.

A major function of surgical bandages and/or packing material is the adsorption of exudate including blood, other fluids and including proteins and the like capable of supporting growth of bacteria, viruses and other pathogens. This can result in serious infection and harmful toxin releases requiring constant changing of the bandages material and treatment with disinfectants and/or antibiotics for limiting growth of pathogens, or the killing thereof.

FIELD OF THE INVENTION

The present invention is related to the medical products and personal care products and especially to anti-germicidal disinfectant delivery, germicidal bandages and tampon/sanitary napkin materials and "bedsore" sheets.

Prior to Lister's discoveries regarding disinfection and the subsequent adoption of sterile bandage material for wound dressings, the "medical art" was barbarous at best. Since Lister's work, a continuing problem has been the propensity for micro-organisms to grow in once sterile bandage material.

A major function of surgical bandages and packing material is the absorption of various excreted fluids or exudate. These fluids are frequently rich in nutrients and are capable of supporting abundant bacterial growth. Since the skin surface or a surgical or wound opening is rarely free of bacteria, the traditional bandage material soon will support a growing bacterial population. This can cause serious infections and harmful toxin releases. Changing the bandage helps somewhat, but treating the bandage material with some type of disinfectant is better for limiting bacterial growth.

The foregoing mentioned U.S. Pat. No. 5,811,471 discusses that the difficulty of producing an effective disinfectant that does not readily wash out of a sponge of polyvinyl alcohol-acetal copolymer led to a washing stage to remove "free dye," leaving only "bound dye." The patent also describes the "toxic shock syndrome" due to dangerous bacterial growth, i.e., staph infection and the patent also documents the "publication tracks" in U.S. patents, etc., of similar efforts to making the "best bandage." In all cases, there was an inherent avoidance of somehow introducing the dye into the wound. There was a general "fear" of leaching of the dye into living tissue.

OBJECTS AND SUMMARY OF THE INVENTION

Therefore, it is an object of the present invention to provide an absorbent material with germicidal properties for use in cleansing wipes, bandages, surgical packings, sanitary napkins, tampons, "bedsore" sheets and other like devices, which ideally absorb bodily fluids, such as wound exudate, without supporting bacterial growth.

It is another objective of the present invention to provide a germicidal material that retains activity even in the presence of blood and protein; and it is a further objective of the current invention that the germicide be available as "free dye" in a specially "loaded" concentration so that a controlled, delivered release of germicide into the wound is accomplished as early as possible to maximize the antitoxin activity when the toxins, i.e., bacteria, viruses, fungi, molds and yeasts, are at their highest concentrations. Another demonstrated and "reduced to practice" objective is that minimal levels of "free-dye" make it possible for the same "loaded pad" to be used for delivery of the "quat-salt" dye and absorption of wound exudates.

It is an additional objective of the present invention that there are "mixed signals" in the literature as to the "toxicity" of gentian violet, which has led to this pervasive fear to try something different. An alternate "delivery system" for the early detoxing step can be provided by a spray bottle to "spritz" a solution of gentian violet directly into the wound, followed by a hydrophilic polyurethane pad containing only "bound dye" to absorb the resulting exudate. This pad can also have an opaque or transparent sheet of hydrophobic polyurethane bonded to the back edges of the sponge with a pressure sensitive adhesive (PSA) so the exudate can be viewed as it moves through the sponge-like pad.

These and additional objectives that will become apparent to one of ordinary skill in the art upon reading the following specification are provided through the use of a sponge-like matrix of hydrophilic polyurethane which contains a germicidal disinfectant dye, particularly gentian violet, which can either be totally "bound" or a combination of "bound" and "free" dye.

Further, the use of glycerin as a co-solvent with water provides a humectant for retaining low levels of water so that germicidal bandage replacement and maintenance becomes less frequent, more effective and economically favorable. The current invention found that more gentian violet is bound to the pad when glycerin is present, thereby allowing for use of a reduced amount of gentian violet and eliminating or greatly minimizing undesirable staining.

DETAILED DESCRIPTION OF THE PREFERRED EMBODIMENTS

The following descriptions are provided to enable any person skilled in the art to make and use the invention and sets forth the best modes contemplated by the inventors for carrying out the invention. Various modifications, however, will remain readily apparent to those skilled in the art, since the generic principles of the present invention have been defined herein specifically to provide a method of using hydrophilic polyurethane foam sponges containing disinfectant dye, i.e., totally "bound" or "bound" with some "free" dye. The latter is used as a controlled delivery system to introduce the germicidal dye to the maximum level of pathogens in a wound. The former is meant as a follow-up pad for absorbing the usual exudate oozing from the wound, while preventing any airborne or other source pathogens from entering a sterilized wound. A single "loaded pad" may be used to both deliver the free-dye to kill the pathogens and absorb the wound exudate, if the excess "free-dye" is kept at a minimum.

By "disinfectant dyes" are meant any of a number of organic dyes, generally known as "vital dyes," including methylene blue and related thionine dyes (electronegative or acidic), acridine orange, acridine yellow and related acriflavine (acridine) dyes (electropositive or basic), quinacrine and its derivatives, gentian violet, brilliant green, malachite green and related triphenyl methane dyes (electropositive) and bis-naphthalene dyes such as trypan blue and trypan red. Methyl blue is a triphenyl methane dye that is amphoteric, an acidic "quat-salt." Generally the dyes show differential activity towards gram-negative versus gram-positive bacteria with electronegative (acidic) dyes, like methylene blue, being more effective on gram-negative bacteria, like *E. Coli* and *Salmonella*, and electropositive (basic) dyes, like gentian violet, being more effective on gram-positive bacteria such as *Staphylococcus* and *Streptococcus*. The following embodiments will be discussed for the gentian violet disinfectant dye alone, however.

The disinfectant property of gentian violet is known, Nucleic acids are macromolecules (polynucleotides) found in all living cells, which are of fundamental importance in controlling the metabolism of living systems. Nucleic acids occur in close association with proteins that form nucleoproteins. The three components of nucleic acid are: purine and pyrimidine bases, a sugar, and phosphoric acid. Gentian violet (crystal violet) not only stains microorganisms, but also inhibits their growth i.e., kills them. Gentian violet is a "chemical bullet" toward toxins. The dye is used as a topical antiseptic. Its action is based on the binding of the positively-charged (quat-salt) dye molecule to the negatively-charged phosphate groups of skin nucleic acids. Because the phosphate sites on the nucleic acids in a wound are the same ones attacked by bacteria, fungi and viruses, the gentian violet competes with the toxins for the sites but more importantly, the toxins have their own nucleic acid phosphates attacked by the dye, thus stopping an infection in its tracks. This is one reason why the rapid delivery of "free" dye into a wound site, as proposed in the present invention, can be of prime importance for rapid healing, depending upon the type of wound and any infection that may be occurring.

The preferred hydrophilic polyurethane is a copolymer of the catalyzed reaction between a di-isocyanate and a polyol and a glycol extender. The preferred material for use in the present invention is a medical grade of the polymer that is already widely used as surgical sponges and packings. It has a uniform pore size and releases neither inherent fines nor solutes. This material is available in various densities, pores, shapes and sizes. It also is available with a transparent backing sheet of hydrophobic polyurethane, that is bonded to the back surface of the sponge, so exudate can be viewed as it rises through the pad. The backing sheet for "bedsore" sheeting is preferably water impervious polyethylene.

Like PVA, hydrophilic polyurethane is able to bind many electronegative as well as electropositive dyes.

The antimicrobial material of the present invention is produced by binding an effective quantity of gentian violet to an appropriate hydrophilic polyurethane substrate. An appropriate substrate means such material with sufficient porosity, or density and absorbency for a particular task. For example, a simple bandage might best use a material that is quite porous and, hence, rather light weight and flexible as would be useful as a cleansing wipe. A one inch thick pad would suffice. As a wound exudate absorber, a ¼ (0.25) inch thick pad would be better, and preferred, especially if it is to be left on the wound site for several days. Tampons, however, might best use somewhat denser, highly absorbent grade of the hydrophilic polyurethane material. An appropriate pad with only "bound" gentian violet could be jelly-rolled into a clean white pad to totally insulate the gentian violet from the vaginal walls. The number and size of air bubbles in the material controls these absorption properties. Hydrophilic polyurethane is already used in orifice and surgical packings. The same grade of material can be used for those applications with the current invention. "Effective quantity" means enough dye to inhibit bacterial growth over the projected period of use. Longer contact of the material with the human body will generally require a higher concentration of dye.

Generally, it is sufficient to soak the HP material in an excess volume of gentian violet solution while squeezing out the entrained air bubbles from the submerged HP pad, and then allowing the gentian violet solution to refill the pores. The original dry pad gets larger, e.g., 4×4 to 5.5×5.5 inches and 5×5 to 6.5×6.5 inches when swelled. When only water is used as the solvent, the drying occurs at the edges of the pad first leaving a puckered "moist" center. After blotting and several days of air drying the pad returns to its original size and is almost totally flat.

In a preferred form of the invention, a combination of water and glycerin is used as the solvent and is mixed with gentian violet and/or other disinfectants; drying of the treated pad occurs uniformly, but because the glycerin is occupying most of the voids, the pad is softer, feels slightly moist and is flat with almost no pucker. The level of "bound" dye can be precalculated and complete absence of blue color from gentian violet in the bath indicates all the absorbed gentian violet is "bound." Conversely, a blue color remaining in the bath after soaking and squeezing indicates the presence of "free" dye. Minimal levels of "free-dye" make possible the use of the same loaded pad to be used for both delivery and adsorption. Glycerin left in the hydrophilic polyurethane helps maintain softness and improve future fluid uptake, after the material is dried. This dual directional flow comprises a particularly important feature of the present invention.

The gentian violet utilized in the present invention will kill gram positive cocci, e.g., *staphylococcus, streptococcus*, and *enterococcus* and gram positive rods, e.g., *corynebacterium, listeria, bacillus, clostridium, actinomyces, Nocardia*, and viruses that cause herpes and shingles. If there is a possibility of gram negative cocci, e.g., *neisseria* and gram negative rods, e.g. *escherichia coli* and *salmonella*, then methylene blue is added to the dye mixture.

Both methylene blue and gentian violet have a long history of topical use. They are generally non-irritating and preliminary experiments indicate that dyed HP is also non-irritating. The inventors have found that hydrophilic polyurethane does bind both positive and negative dyes. It has also been found that a water/glycerin bath of dye yields a flatter, easier to work with pad that is easier to re-wet with water due to the presence of the polar, humectant, "sugar-like" glycerin. This stage can be readily incorporated into the polymer forming process or tolled out to a contractor to provide dry, dye-loaded, sterile-sealed packets for delivery to the customer, user, or patient.

The following clinical experiences highlight the merits of the present invention:

In the course of treating a patient with liquid gentian violet solution at a one percent (1%) strength, the following occurred. The painted wound area of the patient was stained purple by the gentian violet dye. In addition, a scab was formed and the gentian violet became part of the scab. The wound was washed daily with soap and water, which did not seem to affect the scab, and gentian violet was again applied on the existing scab on a daily basis.

After a week, the scab appeared unchanged and the size of the wound remained the same. There was no evidence of any infection.

A change in the procedure was made. Instead of the direct application of the 1% gentian violet solution, a polyurethane pad, containing a reduced amount of gentian violet, mixed with glycerin and water, and then dried, was applied to the wound covered by the scab. Daily washings were continued and the scab was eventually debrided. As the pad containing the gentian violet mixture was applied daily after washings, further staining of the skin by the gentian violet did not occur, and no new scab formed. The wound remained clean with no apparent infection. The wound epithelialization occurred within three to four days with concurrent noticeable decrease in the size and depth of the wound.

In the treatment of a second patient, a polyurethane pad containing the gentian violet mixture was applied to an opened shingle blister caused by a varicella virus. Surprisingly, the wound became dry and appeared to be healing within 24 to 48 hours. Normally, these blistered areas remain weeping for a longer period of time. In view of these results, an apparent possibility exists of applying this medicated pad to opened blisters caused by other types of viral infections, i.e., herpes, smallpox, etc., and to a variety of wounds including, but not limited to, burns caused by radiation or other trauma.

The materials to be used in the presently preferred process and mode are:

Two different types of pads have been tested, namely, a pad made of polyurethane foam; and a Smith and Nephew (Allevyn) hydrophilic polyurethane dressing that consists of an absorbent pad disposed in-between a perforated non-stick, i.e., easy release, layer on the wound contact side and an outer waterproof film.

It is also contemplated that future use will include the Smith and Nephew hydrophilic polyurethane dressing without the outer waterproof film so that the pad will consist only of the non-stick layer on the wound contact side and the polyurethane pad.

Embedding Medication into the Pads:

Research on the present invention indicates that there is a range in the concentration of gentian violet that can be used in the pad. This range is from one drop of gentian violet to the number of drops needed to cause the pad to stain the wound. Dual directional activity is the objective. The volume of medication used is in balance so that the medication can be released into the wound, but yet have enough space left open so that the pad will adequately absorb the exudate. Over saturation through use of an incorrect volume of the medication formula, i.e., the gentian violet, glycerin and water, could block the delivery of the medication or could impede the absorption of the exudate.

A very useful and preferred formulation, for preparation of a polyurethane foam pad of approximately eight (8.0") inches square and ¼ (0.25) inch thick (20.3 cm square by 0.635 cm thick), is a solution comprised of 8 drops of 2 percent (2%) gentian violet, 30 cc. of glycerin, and 450 cc. of water. The pad is soaked in the solution, then removed and squeezed to remove excess liquid and then air dried. The untreated pad weighs approximately 30 g. dry, 270-290 g. saturated, about 130 g. after being wrung out, and about 40 g. after being air dried.

A second solution mixture that has been tested for preparing a pad is comprised of 1⅞ cups (15 ounces) of distilled water, ⅛ cup (one ounce) of glycerin, and 6 to 10 drops of 1% gentian violet. The small amount of gentian violet reduces the possibility of undesirable staining.

Thus, it is seen that the invention including the medicated polyurethane pad, and the novel medical procedure provides a new way of delivering gentian violet to a wound without staining the skin, dressings, sheets, clothes, etc.

In a preferred form of the invention, it is the combination of the pad and diluted gentian violet mixture that provides the correct environment that is needed to promote wound healing. The pad functions to absorb exudate, prevent scab formation, and provide the wound with continual exposure to the antibacterial properties and other attributes of gentian violet. It is the combination of these properties that promotes wound epithelialization and wound healing.

A primary feature of the present invention is that it successfully combines polyurethane foam treated with a compound of gentian violet, water and glycerin to provide a medical dressing that is unique and outperforms other known medical dressings.

Characteristics that Make the Dressing Unique Include:

a. The treated dressing kills fungi, bacteria including methicillin resistant staph aureus and various viruses including those that cause herpes and shingles, thus allowing the treated dressing to be used on infected wounds.

b. These medicated pads treated with gentian violet do not cause the staining that is the usual result of using gentian violet.

c. Using the adjusted gentian violet formulation, along with other chemicals, provides faster healing than in its original, unadulterated form.

d. The new gentian violet formulations eliminate the scabbing over a chronic wound that can impede healing.

e. The polyurethane pad or dressing comprises a soft sponge that does not require moistening before it is applied to the wound and readily conforms to body curvatures of the patient.

When in use, the treated pad is applied directly to the wound and acts as a permeable membrane. It is dual directional in its actions. Upon placement of the pad on the wound, the medication is released into the wound and attacks any pathogen. As the exudate is formed in the wound, it is extracted from the wound by being absorbed into the pad. The dressing usually can be left on the wound for three to four days at a time, saving nursing time with wound care. The pads on certain wounds, or pads being used to prevent bedsores, can be left for a week before they need to be changed.

Further, gentian violet pads treated as set out above reduce scarring. By not removing and changing the pad repeatedly from a wound as must be done with ordinary dressings, the epithelialization is allowed to occur less encumbered.

Still further, when used as a postoperative dressing, the treated pad not only will act as a sanitary barrier protecting the wound, but also will promote wound healing by its dual directions properties. The treated pad, prepared with gentian violet, water and glycerin, rarely adheres to a wound regardless of its size or depth. This ease in removing the pad allows the wound to be easily inspected and covered over again.

Also, the pad treated in accord with the present invention can be used in prevention of pressure sores. The pad can be prophylactically placed over pressure points, which will help prevent pressure sores from forming. If any area of the skin breaks down, the medication in the pad helps prevent the sore from getting infected and helps the wound heal. The pad is also skin friendly and helps normal skin remain healthy.

Many alterations and modifications may be made by those having ordinary skill in the art without departing from the spirit and scope of the present invention. Prior and patented published work however, does not include the utilization of the "free" dye-containing pad to initially overwhelm the pathogens in a wound as quickly as possible to speed up the formation and migration of the exudate to heal the wound sooner. Nor do earlier investigators mention the method of attack of the "quat-salt" dye onto the nucleic acid through the phosphoric acid sites to kill the pathogens of not only bacteria but also fungi, viruses and molds, warts, etc.

The illustrated embodiments of the invention have been set forth only for the purposes of example and should not be taken as limiting the invention. Therefore, it is to be understood that, within the scope of the appended claims, the current invention may be practiced other than as specifically described herein. The "quat-salt" chemical tie to nucleic acid's phosphoric acid site provides a new way to look at viruses, e.g. HIV/AIDS and tumor obliteration.

The invention claimed is:

1. A process for making an antimicrobial, absorbent, medical pad, comprising a hydrophilic polyurethane sponge incorporating a disinfectant dye material, said process including the steps of submerging a hydrophilic polyurethane sponge into a solution of disinfectant dye comprised of gentian violet having a strength in the range of 1 to 3 percent, approximately 30 cc of glycerin and approximately 450 cc of water for treating a sponge having a volume of approximately 256 cc, squeezing entrained air bubbles out of voids in said sponge while submerged to maximize solution and dye incorporation; removing said sponge from said solution and drying said sponge for producing said antimicrobial absorbent pad.

2. The process in claim 1, wherein said solution includes approximately eight drops of gentian violet of one-percent strength.

3. The process in claim 1, wherein said sponge is secured to a transparent backing film comprised of water-impervious polyethylene bonded to said sponge with a pressure sensitive adhesive.

4. A medical pad including medicaments for treating, protecting and healing wounds, said pad being in the form of a foam sponge material constructed from polyurethane and having hydrophilic properties, said pad having been treated with a solution comprised of a medicament, and a solvent therefor, said solvent including approximately 450 cc of water and approximately 30 cc of glycerin for a pad having a volume of approximately 260 cc, said medicament being comprised of approximately six to 10 drops of gentian violet having a strength in the range of 1 to three percent, and said water being removed from said pad for increasing absorbency thereof, whereby undesirable staining of skin, dressings, sheets and clothes is reduced or avoided during use of said pad.

5. A medical pad as defined in claim 4 including a transparent backing film comprised of water-impervious polyethylene bonded to said sponge with a pressure sensitive adhesive.

6. A process for making an antimicrobial, absorbent, medical pad, said pad comprising a hydrophilic polyurethane sponge incorporating as a disinfectant dye gentian violet, the process being characterized by the steps of: submerging said sponge and soaking it in a solution of disinfectant dye, glycerin and water, wherein for treating a polyurethane sponge with a volume of approximately 256 cc (400 $cm^2 \times 0.64$ cm), said solution contains either 8 drops of disinfectant dye of two-percent strength gentian violet, or between 6 and 10 drops of disinfectant dye of one-percent strength gentian violet, and approximately 30 cc of glycerin, and approximately 450 cc water; removing said sponge from said solution; squeezing the sponge to remove excess liquid: and air drying said sponge.

* * * * *